United States Patent [19]

Regnier et al.

[11] Patent Number: 5,206,247
[45] Date of Patent: Apr. 27, 1993

[54] SPIRO(4.5.)DECANE COMPOUNDS

[75] Inventors: Gilbert Regnier, Chatenay Malabry; Claude Guillonneau, Clamart; Jean-Paul Vilaine, Chatenay; Albert Lenaers, Triel Sur Seine; Jean-Pierre Iliou, Puteaux, all of France

[73] Assignee: Adir Et Compagnie, Courbevoie, France

[21] Appl. No.: 755,155

[22] Filed: Sep. 5, 1991

[30] Foreign Application Priority Data

Sep. 6, 1990 [FR] France ............................ 90 11044

[51] Int. Cl.$^5$ ...................... A61R 31/44; C07D 221/20
[52] U.S. Cl. ........................................ 514/278; 546/16
[58] Field of Search .................... 546/16, 19; 514/218

[56] References Cited

U.S. PATENT DOCUMENTS 3,399,192  8/1968  Regnier ................................ 546/19
4,244,961  1/1981  Kluge .................................. 546/16

FOREIGN PATENT DOCUMENTS 292400  11/1988  European Pat. Off. .............. 546/19
2609245  9/1976  Fed. Rep. of Germany ........ 546/16

OTHER PUBLICATIONS

Diplock et al. "Vitamine E . . . " Ann. New York Aca. Sci. vol. 570, pp. 4–5 (1989) Lee Atherosclerosis.
Ann. New York Aca. Sci. vol. 454 pp. 46–48 (1985) Caroon et al "Synthesis and antihypertensive . . . " J. Med Chem. 24, 1320–1328 (1981).
Steinberg; Atherosclerosis Review 1988; eds Stokes & Mancini Raven, New York, vol. 18, 1–23, Steinberg et al, N. Engl. J. Med. 1989; 320: 915–924.
Palinski et al, PNAS 1989; 86, 1372–2376, Yla-Herttuala, Circulation 1989; 80 II–160.
Kita et al, PNAS 1987; 84, 5928–5931.
Carew et al, PNAS 1987; 84, 7725–7729.
Riemersma et al, Lancet 1991; 337, 1–5.
Regnström et al, Lancet 1992; 339, 1184–1186.

*Primary Examiner*—C. Warren Ivy
*Assistant Examiner*—Celia Chang
*Attorney, Agent, or Firm*—Gordon W. Hueschen

[57]  ABSTRACT

The compounds are 8-substituted 1-oxa-2-oxo-3,8-diazaspiro [4.5]decanes useful for the treatment of dyslipidaemiae, atherosclerosis and pathologies in which membrane lipid peroxidation plays an initiating and/or aggravating role.

A compound disclosed is (R,S)-8-[3(3,5-di-tert.-butyl-4-hydroxyphenylthio)-2-hydroxypropyl]-1-oxa-2oxo-3,8-diazaspiro [4.5]decane.

9 Claims, No Drawings

SPIRO(4.5.)DECANE COMPOUNDS

The present invention relates to spiro[4.5; ]decane compounds of formula I:

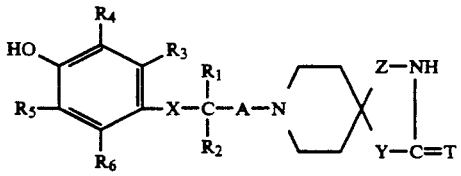

in which:

X represents an oxygen atom, a sulphur atom;

A represents a straight-chain or branched hydrocarbon radical containing from 2 to 10 carbon atoms that optionally contains a double bond and/or is optionally substituted by a hydroxy radical;

Y represents an oxygen atom, a sulphur atom or a $CH_2$ radical;

T represents an oxygen atom or a sulphur atom,

Z represents:
either a group $CH-R_7$ in which $R_7$ represents a hydrogen atom or an alkyl radical containing from 1 to 3 carbon atoms,
or a carbonyl group;

$R_1$ and $R_3$:
each simultaneously represents a hydrogen atom,
together form a $(CH_2)_n$ bridge in which n is 1 or 2, or
$R_1$ represents a methyl radical and simultaneously
$R_3$ represents a hydrogen atom;

$R_2$ and $R_6$, which are the same or different, each represents a hydrogen atom or a methyl radical, and $R_4$ and $R_5$, which are the same or different, each represents a straight-chain or branched alkyl radical containing from 1 to 6 carbon atoms.

The prior art in this field is illustrated especially by the following:

French Patent No. 1 441 575, which relates to spiro[4.5]decane compounds of the formula:

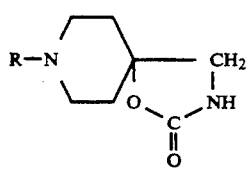

in which R represent, inter alia, an Ar-A'- group in which Ar may be especially a phenyl radical that is mono or di-substituted by hydroxy or alkyl radicals; and A' may be especially an —O—$CH_2$—$CH_2$ chain;

and Special Medicament Patent No. 4463 M, which mentions the analgesic, anti-inflammatory and broncholytic properties of the said compounds, as well as their use as medicaments for the treatment of inflammatory conditions, bronchospasms and pain.

Modifications to the structure, in particular to the substituent R, resulted in the compounds (I) of the present invention, which differ from the closest compounds of the prior art not only in their chemical structure but also in their pharmacological profile, as well as their therapeutic use, as demonstrated by the pharmacological study given as an example hereinafter.

The present invention relates also to a process for the preparation of compounds of the general formula I which is characterised in that:
a compound of the general formula II:

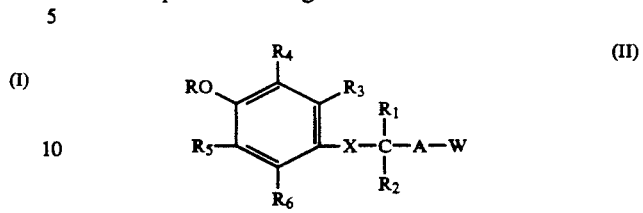

in which:

X, A, $R_1$, $R_2$, $R_3$, $R_4$, $R_5$ and $R_6$ are as defined hereinbefore,

W represents a chlorine or bromine atom or a tosyloxy radical, and

R represents a hydrogen atom or a readily hydrolysable protecting group, such as an acylated or silylated group, is condensed with a compound of the general formula III:

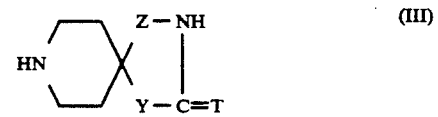

in which Y, Z and T are as defined hereinbefore;

and, when R is other than hydrogen, the compound so obtained is hydrolysed.

The condensation of compounds II and III is carried out particularly advantageously in a suitable solvent such as, for example, acetonitrile, methyl ethyl ketone, tetrahydrofuran, dimethylformamide, ethanol or propanol, at a temperature of from 80° to 120° C., in the presence of an acceptor for the acid formed during the course of the reaction. There may be used as acceptor, for example, an alkali metal carbonate, triethylamine or an excess of the compound of formula III used in the reaction.

The resulting compounds may be purified by flash chromatography on silica (35–70μ) using as eluant: $H_3CCOOC_2H_5$ or $CH_2Cl_2/CH_3OH$, for example, or by the formulation of salts and crystallisation thereof.

The starting materials of formulae II and III used in the process described above are either known compounds, or compounds prepared from known substances in accordance with processes described in the literature for the preparation of analogous compounds.

The compounds of the general formula I yield salts with physiologically tolerable acids, which salts as such are included in the present invention.

Furthermore if, in formula I, $R_1$ is different from $R_2$, and/or $R_7$ is other than a hydrogen atom, and/or A is a branched chain, there exists, depending on the case in question, one or more chiralities, which has the result that the compounds I are in the form of enantiomers or diastereoisomers, which also form part of the present invention.

The compounds of the present invention have valuable therapeutic and pharmacological properties. In particular it has been demonstrated that, on the one hand, these compounds have the capacity to protect human LDLs (low density lipoproteins that bring about the transport of cholesterol) in vitro and ex vivo with respect to oxidative modifications induced by copper and by endothelial cells and that, on the other hand, they have a protective effect in vitro on the oxidative necrosis of cardiac cells.

Oxidative modifications of LDLs at present appear to constitute a significant mechanism in the formation and the extension of atheromatous vascular lesions. Also, the anti-oxidant properties of the compounds of the present invention, especially with respect to LDLs, enables them to be used as medicaments in the treatment of:

dyslipidaemiae, for preventing especially vascular complications, atherosclerosis with its different cerebral, coronary, peripheral vascular localisations, and also pathologies in which membrane lipid peroxidation plays an initiating or aggravating role, such as ischaemic cardiopathies, reperfusion of organs, including transplanted organs, traumatic or degenerative ischaemic pathologies of the central or peripheral nervous system, chronic or acute inflammatory disorders and auto-immune diseases.

The present invention relates also to pharmaceutical composition comprising as active ingredient a compound of the general formula I or a physiologically tolerable salt thereof, in admixture or association with an appropriate pharmaceutical exicipient, such as, for example, glucose, lactose, starch, talc, ethyl cellulose, magnesium stearate or cocoa butter.

Those pharamceutical compositions are generally in dosage form and may comprise from 5 to 250 mg of active ingredient.

They may be, for example, in the form of tablets, dragees, soft gelatin capsules, suppositories, injectable or drinkable solutions and, depending on the case in question, may be administered orally, rectally or parenterally at a dosage of from 5 to 500 mg in 1 or 2 daily doses.

The following Examples illustrate the present invention: melting points are determined using a Köfler hot plate (K) or a capillary tube (cap.).

EXAMPLE 1

(R,S)-8-[3-(3,5-di-tert.-butyl-4-hydroxyphenylthio)-2-hydropropyl]-1-oxa-2-oxo-3,8-diazaspiro[4.5]decane:

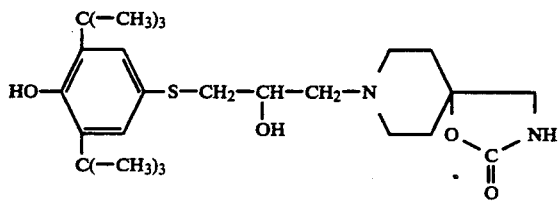

A suspension of 6.5 g of 3-(3,5-di-tert.-butyl-4-hydroxyphenylthio)-2-hydroxy-1-hydroxy-1-chloropropane, melting (K) at 68° C., and 9 g of 1-oxa-2-oxo-3,8-diazaspiro [4.5] decane melting (K) at 202° C., in 200 ml of acetonitrile is heated under reflux for 20 hours in the presence of 0.5 g of potassium iodide.

When the reaction is complete, the mixture is cooled and the insoluble salt is removed by filtration. The solution is evaporated and the residue is dissolved in CH₂Cl₂. The resulting solution is washed with H₂O and 10 % NaHCO₃. After evaporation, chromatography on silica is carried out using CH₂Cl₂/CH₃OH (95/5) as eluant. Evaporation of the eluates yields 4 g of (R,S)-8-[3-(3,5-di-tert.-butyl-4-hydroxyphenylthio)-2-hydroxypropyl]-1-oxa-2-oxo-3,8-diazaspiro[4.5]decane in the form of beige crystals melting (K) at 170° C.

The chlorinated starting compound was prepared by reacting epichlorohydrin with 3,5-di-tert.-butyl-4-hydroxythiophenol in tetrahydrofuran in the presence of BH₄N⊕F⊖ as catalyst.

EXAMPLE 2

8-[3-(2,3,5-trimethyl-4-hydroxyphenoxy)propyl]-1-oxa-2-oxo-3,8-diazaspiro[4.5]decane:

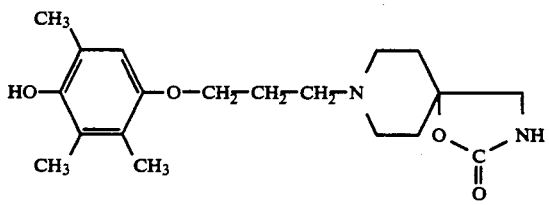

A solution of 5.04 g of 3-(4-acetoxy-2,3,5-trimethylphenoxy)-1-bromopropane melting (K) at 54° C. and 5 g of 1-oxa-2-oxo-3,8-diazaspiro[4.5]decane in 300 ml of acetonitrile is heated under reflux for 20 hours in the presence of 1.2 g of potassium iodide. When the reaction is complete, the solvent is evaporated off under reduced pressure and the residue is taken up in 10 % NaHCO₃ and CH₂Cl₂. The organic layer is decanted off and washed several times with water.

After evaporating off the solvent, the residue is chromatographed on 300 g of silica and eluted with the system CH₂Cl₂/CH₃OH (93/7). Evaporation of the eluates yields 5.2 g of the acetylated product in the form of an oil.

4.57 g of that product dissolved in 120 ml of ethanol are hydrolysed with 47 ml of 4N HCl by heating under reflux for two hours. After evaporation of the solvent, the residue is taken up in CH₂Cl₂ and 10 % NaHCO₃ and the organic phase is decanted off and evaporated.

Purification by chromatography on 200 g of silica using CH₂Cl₂/CH₃OH (90/10) as eluant, followed by evaporation of the eluates, yields 3.6 g of 8-[3-(2,3,5-trimethyl-4-hydroxyphenoxy)propyl]-1-oxa-2-oxo-3,8-diazaspiro-[4.5]decane crystals melting (K) at 155° C.

EXAMPLES 3 TO 36

The compounds of the Examples listed in the following Table I were prepared by proceeding as described in Example 1:

TABLE I

Compounds of formula I:

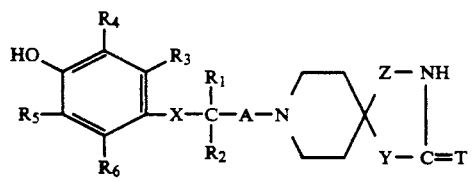

(I)

| Example No | X | A | $R_1$ | $R_3$ | $R_2$ | $R_6$ | $R_4$ | $R_5$ | Y | T | Z | M.P.(°C.) |
|---|---|---|---|---|---|---|---|---|---|---|---|---|
| 3 | S | $(CH_2)_2$ | H | H | H | H | $-C(CH_3)_3$ | $-C(CH_3)_3$ | O | O | $CH_2$ | (K) 152 |
| 4 | S | $(CH_2)_4$ | H | H | H | H | $-C(CH_3)_3$ | $-C(CH_3)_3$ | O | O | $CH_2$ | (K) 146 |
| 5 | O | $(CH_2)_4$ | H | H | H | H | $-C(CH_3)_3$ | $-C(CH_3)_3$ | O | O | $CH_2$ | (K) 166 |
| 6 | O | $(CH_2)_2$ | H | H | H | H | $-C(CH_3)_3$ | $-C(CH_3)_3$ | O | O | $CH_2$ | (K) 192 |
| 7 | O | $-CH-CH_2$ \| $OH$ | H | H | H | H | $-C(CH_3)_3$ | $-C(CH_3)_3$ | O | O | $CH_2$ | (K) 200 |
| 8 | O | $-CH-CH_2$ \| $OH$ | H | H | H | H | $-C(CH_3)_3$ | $-C(CH_3)_3$ | O | S | $CH_2$ | (Meringue = Amorphous) |
| 9 | S | $-CH-CH_2$ \| $OH$ | H | H | H | H | $-C(CH_3)_3$ | $-C(CH_3)_3$ | O | S | $CH_2$ | (Amorphous) |
| 10 | O | $(CH_2)_2$ | H | H | H | H | $-C(CH_3)_3$ | $-C(CH_3)_3$ | O | S | $CH_2$ | (Amorphous) |
| 11 | O | $-CH-CH_2$ \| $OH$ | H | H | H | H | $-C(CH_3)_3$ | $-C(CH_3)_3$ | $CH_2$ | O | $C=O$ | (Amorphous) |
| 12 | S | $-CH-CH_2$ \| $OH$ | H | H | H | H | $-C(CH_3)_3$ | $-C(CH_3)_3$ | $CH_2$ | O | $C=O$ | (Amorphous) |
| 13 | S | $(CH_2)_2$ | H | H | H | H | $-C(CH_3)_3$ | $-C(CH_3)_3$ | O | S | $CH_2$ | |
| 14 | O | $(CH_2)_2$ | H | H | H | H | $-C(CH_3)_3$ | $-C(CH_3)_3$ | $CH_2$ | O | $C=O$ | |
| 15 | S | $(CH_2)_2$ | H | H | H | H | $-C(CH_3)_3$ | $-C(CH_3)_3$ | $CH_2$ | O | $C=O$ | |
| 16 | O | $(CH_2)_2$ | H | H | H | H | $-C(CH_3)_3$ | $-C(CH_3)_3$ | O | O | $CH_3$ \| $-CH-$ | |
| 17 | S | $(CH_2)_2$ | H | H | H | H | $-C(CH_3)_3$ | $-C(CH_3)_3$ | O | O | $CH_3$ \| $-CH-$ | |
| 18 | O | $-CH-CH_2$ \| $OH$ | H | H | H | H | $-C(CH_3)_3$ | $-C(CH_3)_3$ | O | O | $CH_3$ \| $-CH-$ | |
| 19 | S | $-CH-CH_2$ \| $OH$ | H | H | H | H | $-C(CH_3)_3$ | $-C(CH_3)_3$ | O | O | $CH_3$ \| $-CH-$ | |
| 20 | O | $(CH_2)_2$ | H | H | H | H | $-C(CH_3)_3$ | $-C(CH_3)_3$ | O | O | $C=O$ | |
| 21 | S | $(CH_2)_2$ | H | H | H | H | $-C(CH_3)_3$ | $-C(CH_3)_3$ | O | O | $C=O$ | |
| 22 | O | $-CH-CH_2$ \| $OH$ | H | H | H | H | $-C(CH_3)_3$ | $-C(CH_3)_3$ | O | O | $C=O$ | |
| 23 | S | $-CH-CH_2$ \| $OH$ | H | H | H | H | $-C(CH_3)_3$ | $-C(CH_3)_3$ | O | O | $C=O$ | |
| 24 | O | $(CH_2)_2$ | H | H | H | H | $CH_3$ | $CH_3$ | $CH_3$ | O | O | $CH_2$ |
| 25 | O | $-CH-CH_2$ \| $OH$ | H | H | H | H | $CH_3$ | $CH_3$ | $CH_3$ | O | O | $CH_2$ |
| 26 | O | $(CH_2)_2$ | $CH_3$ | H | $CH_3$ | $CH_3$ | $CH_3$ | $CH_3$ | O | O | $CH_2$ |

TABLE I-continued

Compounds of formula I:

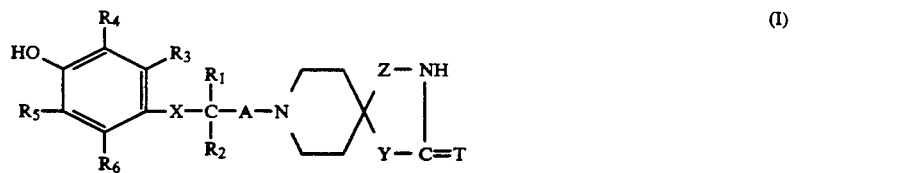

(I)

| Example No | X | A | R₁ | R₃ | R₂ | R₆ | R₄ | R₅ | Y | T | Z | M.P.(°C.) |
|---|---|---|---|---|---|---|---|---|---|---|---|---|
| 27 | O | CH₃<br>\|<br>C—CH₂<br>\|<br>CH₃ | H | H | H | CH₃ | CH₃ | CH₃ | O | O | CH₂ | |
| 28 | O | CH₂ | —(CH₂)₂ | | CH₃ | CH₃ | CH₃ | CH₃ | O | O | CH₂ | |
| 29 | O | CH₂ | —(CH₂)₂ | | CH₃ | CH₃ | CH₃ | CH₃ | O | O | CH₂ | |
| 30 | O | (CH₂)₄ | H | H | H | CH₃ | CH₃ | CH₃ | O | O | CH₂ | (cap)<br>164–165 |
| 31 | S | (CH₂)₂ | CH₃ | H | CH₃ | H | —C(CH₃)₃ | —C(CH₃)₃ | O | O | CH₂ | HCl (cap)<br>250–252 |
| 32 | S | —CH—CH₂<br>\|<br>OH | H | H | H | CH₃ | CH₃ | CH₃ | O | O | CH₂ | (Amorphous) |
| 33 | O | (CH₂)₂ | —(CH₂)₂— | | CH₃ | CH₃ | CH₃ | CH₃ | O | O | CH₂ | (Amorphous) |
| 34 | O | (CH₂)₃ | —(CH₂)₂— | | CH₃ | CH₃ | CH₃ | CH₃ | O | O | CH₂ | (Amorphous) |
| 35 | S | (CH₂)₂ | H | H | H | CH₃ | CH₃ | CH₃ | O | O | CH₂ | (K) 150 |
| 36 | O | (CH₂)₃ | CH₂ | | CH₃ | CH₃ | CH₃ | CH₃ | O | O | CH₂ | |

The starting materials used to prepare the compounds of the present invention are listed in the following Tables II and III:

TABLE II

Compounds of formula II:

(II)

| X | R | R₁ | R₃ | R₂ | R₆ | R₄ | R₅ | A | W | Physical Characteristics | Method of preparation (*) |
|---|---|---|---|---|---|---|---|---|---|---|---|
| O | H | H | H | H | H | —C(CH₃)₃ | —C(CH₃)₃ | (CH₂)₂ | Br | M.P(K) =<br>35–36° C. | 1 |
| O | H | H | H | H | H | —C(CH₃)₃ | —C(CH₃)₃ | (CH₂)₄ | Br | Oil | 1 |
| S | H | H | H | H | H | —C(CH₃)₃ | —C(CH₃)₃ | (CH₂)₂ | Br | Oil | 1 |
| S | H | H | H | H | H | —C(CH₃)₃ | —C(CH₃)₃ | (CH₂)₄ | Br | Oil | 1 |
| S | H | H | H | H | H | —C(CH₃)₃ | —C(CH₃)₃ | CH—CH₂<br>\|<br>OH | Cl | M.P(K) = 68° C. | 1 |
| S | H | H | H | H | H | —C(CH₃)₃ | —C(CH₃)₃ | CH—(CH₂)₂<br>\|<br>OH | Br | M.P(K) =<br>125° C. | 1 |
| O | CH₃<br>\|<br>—Si—C—C(CH₃)₃<br>\|<br>CH₃ | H | H | H | CH₃ | CH₃ | CH₃ | (CH₂)₂ | Br | M.P(cap) =<br>45–46° C. | 2 |
| O | —CO CH₃ | H | H | H | CH₃ | CH₃ | CH₃ | (CH₂)₂ | Br | M.P(K) = 54° C. | 3 |

TABLE II-continued

Compounds of formula II:

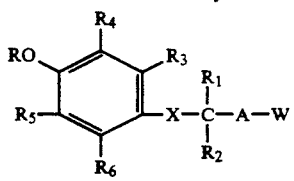

| X | R | $R_1$ | $R_3$ | $R_2$ | $R_6$ | $R_4$ | $R_5$ | A | W | Physical Characteristics | Method of preparation (*) |
|---|---|---|---|---|---|---|---|---|---|---|---|
| O | $-CH_2-O-C_2H_5$ | $(CH_2)_2$ | $CH_3$ | $CH_3$ | $CH_3$ | $CH_3$ | $CH_3$ | $CH_2$ | Tosyloxy | Oil | 4 |

(*) Methods of preparation:

1 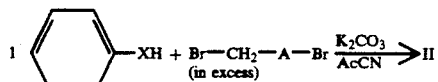

2 T. YOSHIOKA et al. J. Med. Chem. 32, 421-428 (1989)

3 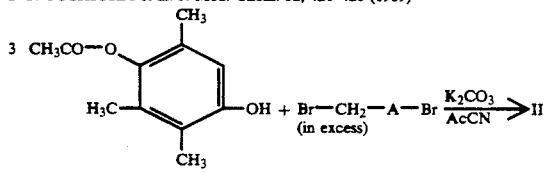

4 Tosylation of the alcohol prepared according to J. SCOTT et al., J. Am. Oil. Chem. Soc. 51, (5), 200-203, (1974)

TABLE III

Compounds of formula III:

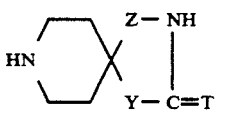

| Y | T | Z | Physical characteristics | Method of preparation |
|---|---|---|---|---|
| O | O | $CH_2$ | M.P(K) = 202° C. | G. REGNIER et al. Chimie Thérap. (1969)(3), 185-194 |
| O | O | $\begin{array}{c}CH_3\\ \vert \\ -CH-\end{array}$ | M.P(cap) = 245-246° C. | J. MAILLARD et al. Chim. Thérap. (1973)(4), 393-397 |
| O | S | $CH_2$ | M.P(K) = 240° C. | Detritylation (HCl) of the corresponding 8-trityl compound M.P(K) = 248-250° C. |
| O | O | C=O | M.P(cap) = 338° C. | Preparation of the 8-benzyl compound according to Y. NAGAI Chem. Pharm. Bull. 24 (6), 1179-1188 (1976) and debenzylation with $H_2$/Pd—C |
| $CH_2$ | O | C=O | M.P(K) = 240° C. | Preparation of the 8-benzyl compound M.P(K): 187° C., from: $C_6H_5-CH_2-N\overset{\diagup COOH}{\underset{\diagdown COOH}{\bigcirc}}$ + urea, according to MC ELVAIN et al. Am. Soc, 71, 901, (1949), and debenzylation with H2/Pd—C |

EXAMPLE 37

Pharmacological Study

The action of the compounds of the present invention was demonstrated using both animal and human LDLs. The inhibitory activity of the compounds as regards oxidative modification of the LDLs, induced by copper sulphate and by endothelial cells of the aorta of a rabbit, was demonstrated both in vitro and after oral administration to Watanabe rabbits. The activity of the compounds was tested by comparison with probucol and vitamin E, which were used as reference products.

1. IN VITRO STUDY

1.1 Materials and Methods 1.1.1. Modification of the LDLs by copper sulphate Human LDLs are incubated for 24 hours in the presence of copper sulphate ($5 \times 10^{-5}$M or $5 \times 10^{-6}$M) and in the absence or presence of the test compounds ($10^{-7}$M to $10^{-4}$M).

After incubation, the peroxidation of the LDLs is evaluated by electrophoresis on agar gel and by the formation of one of the products of lipid peroxidation: malonic dialdehyde (MDA) (Parthasarathy S., Young S. G., Witztum J. L., Pittman R. C., and Steinberg D.; J. Clin. Invest. 77, 641–644, 1986).

The activity of the test compounds is evaluated by calculating the concentrations that reduce the production of MDA by 50% ($IC_{50}$) compared with control experiments carried out in the absence of test compound.

1.1.2. Modification of the LDLs by Endothelial Cells

Human LDLs are incubated for 24 hours in the presence of rabbit aorta endothelial cells (line RECL B4 supplied by Professor Steinberg, USA) and in the absence or presence of the test compounds ($10^{-7}M$ to $10^{-4}M$).

After incubation, the peroxidation of the LDLs is evaluated by electrophoresis on agar gel and by the formation of one of the products of lipid peroxidation: malonic dialdehyde (MDA) (Steinbrecher U.P., Parthasarathy S, Leake D. S., Witztum J. L., and Steinberg D., Proc. Nat. Acad. Sci. USA 81. 3883–3887, 1984).

The activity of the test compounds is evaluated by calculating the concentrations that reduce the production of MDA by 50% ($IC_{50}$) compared with the control experiments carried out in the absence of test compound.

1.1.3. Oxidative Necrosis of Cardiac Cells

Cardiac cells of new-born rats are used between the 5th and 6th days after placing in a culture. Oxidative necrosis is induced by the enzymatic system hypoxanthine (HX, 1 mM) and xanthine oxidase (XO, 10 mU/ml), which produces free radicals. The necrosis is evaluated 4 hours after the addition of XO/HX by the spectrophotometric measurement of the cytosolic α-hydroxybutyrate dehydrogenase (α-HBDH) activity liberated in the supernatant. Two reference molecules (probucol, vitamin E) and 3 molecules representative of the present invention (corresponding to Examples 1, 3 and 4) were tested. The cells are treated with the molecules 16 hours and 1 hour before the beginning of the experiment after renewing the medium. At the beginning of the experiment, the treatment is carried out one last time.

1.2. Results

1.2.1. Effect on the modification of the LDLs

Table A lists the $IC_{50}$ values, which indicate the capacity to inhibit the lipid peroxidation of human LDLs, obtained with a sample of the compounds of the invention and of the reference compounds probucol and vitamin E, in two tests causing the development of the oxidation of the LDLs: by copper sulphate ($Cu^{2+}$) or by endothelial cells (EC).

TABLE A

| COMPOUNDS | IC50(M) $Cu^{2+}$ | EC |
|---|---|---|
| Example 1 | $3 \times 10^{-7}$ | $3 \times 10^{-8}$ |
| Example 3 | $3 \times 10^{-7}$ | $5 \times 10^{-8}$ |
| Example 4 | $8 \times 10^{-7}$ | $2 \times 10^{-8}$ |
| Example 5 | $7 \times 10^{-7}$ | $8 \times 10^{-7}$ |
| Example 6 | $3 \times 10^{-7}$ | $3 \times 10^{-7}$ |
| Example 7 | $2 \times 10^{-6}$ | |
| Example 30 | $3 \times 10^{-7}$ | |
| Example 31 | $8 \times 10^{-7}$ | $2 \times 10^{-8}$ |

TABLE A-continued

| COMPOUNDS | IC50(M) $Cu^{2+}$ | EC |
|---|---|---|
| Example 32 | $3 \times 10^{-7}$ | |
| Example 33 | $3 \times 10^{-7}$ | |
| Example 34 | $3 \times 10^{-7}$ | |
| PROBUCOL | $3 \times 10^{-6}$ | $4 \times 10^{-6}$ |
| VITAMIN E | $>10^{-4}$ | $4 \times 10^{-6}$ |

These results show clearly the greater ability especially of the compounds of Examples 1, 3, 4, 5, 6 and 31 compared with probucol or vitamin E, to protect human LDLs with respect to modifications induced by copper sulphate and endothelial cells.

Those compounds of which the $IC_{50}$ values as regards the peroxidation induced by copper sulphate ($5 \times 10^{-6}M$) are between $3 \times 10^{-7}$ and $8 \times 10^{-7}M$ are 10 times more powerful than probucol in this test; referring to the test using endothelial cells, the compounds in particular of Examples 1, 3, 4 and 32 with $IC_{50}$ values between $2 \times 10^{-8}M$ and $5 \times 10^{-8}M$ prove to be 100 times more powerful than probucol.

1.2.2. Effect on Oxidative Necrosis of Cardiac Cells

Table B lists the indices of the necrosis of cardiac cells induced by the system hypoxanthine/xanthine oxidase on its own or in the presence of increasing concentrations of the compounds of the invention or of the reference compounds: probucol and vitamin E.

The compounds of Examples 1, 3 and 4 (particularly representative of the invention), at concentrations of $10^{-6}M$ and $10^{-5}M$, reduce by more than 80% and 95% respectively, the oxidative necrosis of cardiomyocytes and are distinctly superior to the reference compounds, of which the activity, which is far weaker, is not evident until $10^{-5}M$.

The compound of Example 1 is distinguished especially by a more than 50% protective effect starting from a concentration of $10^{-7}M$.

TABLE B

| | EFFECT ON OXIDATIVE NECROSIS OF CARDIAC CELLS | | | |
|---|---|---|---|---|
| Compounds | control HO + HX | $10^{-7}$ M HO + HX | $10^{-6}$ M HO + HX | $10^{-5}$ M HO + HX |
| vitamin E | 100.0 ± 12.5 | 83.5 ± 8.0 | 79.0 ± 7.4 | 61.1 ± 2.5 |
| probucol | 100.0 ± 6.2 | 103.0 ± 2.0 | 68.8 ± 3.9 | 26.6 ± 6.3 |
| Example 1 | 100.0 ± 6.5 | 42.8 ± 11.3 | 19.1 ± 7.3 | 3.8 ± 1.9 |
| Example 3 | 100.0 ± 12.4 | 60.6 ± 17.1 | 12.0 ± 4.4 | 4.2 ± 2.7 |
| Example 4 | 100.0 ± 6.9 | 79.1 ± 8.0 | 2.1 ± 1.0 | 2.6 ± 0.7 |

The necrosis index 100 corresponds to a liberation of 43.6±1.0% in 4 hours of the cytosolic content of α-HBDH in the supernatant.

The results are expressed in the form of means ± sem ($4 \leq n \leq 5$, 3 repetitions per experiment).

2. EX VIVO STUDY

2.1 Materials and Methods

Watanabe rabbits (generally hyperlipidaemic rabbits) are used that range in weight from 3 kg to 5 kg. The animals are treated orally with the carrier of the test compounds (control group) or with the test compounds at doses of 10, 50 and 250 mg/kg/day for 3 days.

When the treatment is complete, the LDLs of the animals are prepared by ultracentrifugation and subjected to oxidation with copper sulphate ($5 \times 10^{-6}$M). The lipid peroxidation of the LDLs is evaluated after various periods of incubation with copper sulphate (from 2 to 24 hours) by measuring the formation of MDA.

2.2 Results

Table C lists the MDA production values according to the incubation period with copper sulphate of those LDLs originating from the control animals and those originating from the animals treated with the compounds of Examples 1, 3 and 31 at different doses or with probucol.

TABLE C

| | | MDA PRODUCTION (nM/mg proteins) | | | | |
|---|---|---|---|---|---|---|
| | | Period of incubation of the LDLs with copper sulphate (hours) | | | | |
| COMPOUNDS | NUMBER OF ANIMALS | 2 | 4 | 6 | 8 | 24 |
| Control | 6 | 3.31 ± 0.41 | 4.84 ± 0.59 | 13.41 ± 2.29 | 26.04 ± 2.82 | 28.06 ± 2.87 |
| Example 1 250 mg/kg/day | 6 | 0.2 ± 0.2 | 1.27 ± 0.91 | 0 | 0 | 1.02 ± 0.53 |
| Example 3 250 mg/kg/day | 3 | 0.66 ± 0.18 | 0 | 0 | 0.69 ± 0.29 | 0.91 ± 0.16 |
| Example 3 50 mg/kg/day | 3 | 0.16 ± 0.15 | 0 | 1.06 ± 0.29 | 1.44 ± 0.46 | 7.30 ± 1.66 |
| Example 3 10 mg/kg/day | 3 | 1.27 ± 0.10 | 0.27 ± 0.27 | 3.29 ± 0.72 | 6.85 ± 2.22 | 22.78 ± 0.70 |
| Example 31 250 mg/kg/day | 3 | 0.19 ± 0.19 | 0.51 ± 0.31 | 0.16 ± 0.16 | 0.71 ± 0.12 | 0.99 ± 0.15 |
| Example 31 50 mg/kg/day | 3 | 0.33 ± 0.24 | 0.72 ± 0.30 | 1.03 ± 0.47 | 1.04 ± 0.34 | 3.16 ± 0.14 |
| Probucol 250 mg/kg/day | 5 | 1.85 ± 0.27 | 3.50 ± 0.27 | 4.90 ± 0.89 | 12.26 ± 2.45 | 23.81 ± 0.37 |

According to these results, the peroxidation of the LDLs of the Watanabe rabbits treated with probucol is retarded by approximately 2 hours compared with that of the control animals.

By contrast with probucol, under the same experimental conditions, the compounds of Examples 1, 3 and 31 inhibit the peroxidation of the LDLs induced by copper sulphate from a dose of 50 mg/kg/day. Example 3 proves particularly effective starting from a dose of 10 mg/kg/day (cf. Table C).

3. CONCLUSION

The results reported demonstrate, on the one hand, that the compounds of the invention protect human LDLs in vitro with respect to oxidative modifications much more effectively than probucol and vitamin E and, on the other hand, that on oral administration to an animal these compounds, by comparison with probucol, cause far superior protection of the LDLs with a much longer lasting action.

Furthermore, the compounds of the invention also protect cardiac cells more effectively than probucol and vitamin E with respect to oxidative necrosis induced in vitro.

We claim:

1. A compound selected from those of formula I:

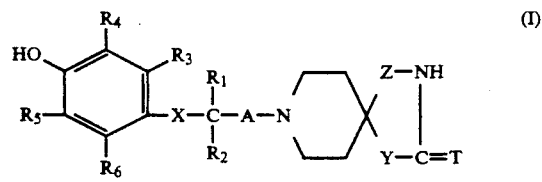

in which:

X represents oxygen or sulphur,

A represents a straight-chain or branched hydrocarbon radical containing 2 to 10 carbon atoms inclusive which optionally contains a double bond and/or is optionally substituted by hydroxy;

Y represents oxygen, sulphur, or $CH_2$;

T represents oxygen or sulphur;

Z represents:

CH-$R_7$ in which $R_7$ represents hydrogen or alkyl containing 1 to 3 carbon atoms, inclusive or carbonyl;

$R_1$ and $R_3$:

each simultaneously represents hydrogen, together form a $(CH_2)_n$ bridge in which n is 1 or 2, or $R_1$ represents methyl and simultaneously $R_3$ represents hydrogen;

$R_2$ and $R_6$, which are the same or different, each represents hydrogen or methyl, and $R_4$ and $R_5$, which are the same or different, each represents a straight-chain or branched alkyl containing 1 to 6 carbon atoms inclusive;

its diastereoisomers and enantiomers, as well as its addition salts with a physiologically-tolerable acid.

2. A compound of claim 1 which is:

(R,S)-8-[3-(3,5-di-tert.-butyl-4-hydroxyphenylthio)-2-hydroxypropyl]-1-oxa-2-oxo-3,8-diazaspiro[4.5]-decane.

3. A compound of claim 1 which is:

8-[3-(3,5-di-tert.-butyl-4-hydroxyphenylthio)-propyl-]-1--oxa-2-oxo-3,8-diazaspiro[4.5]decane.

4. A compound of claim 1 which is:

8-[5-(3,5-di-tert.-butyl-4-hydroxyphenylthio)-pentyl]-1-oxa-2-oxo-3,8-diazaspiro[4.5]decane.

5. A compound of claim 1 which is:

8-[5-(3,5-di-tert.-butyl-4-hydroxyphenoxy)-pentyl]-1-oxa-2-oxo-3,8-diazaspiro[4.5]decane.

6. A compound of claim 1 which is:

8-[3-(3,5-di-tert.-butyl-4-hydroxyphenoxy)-propyl]-1-oxa-2-oxo-3,8-diazaspiro[4.5]decane.

7. A compound of claim 1 which is:

8-[3-(3,5-di-tert.-butyl-4-hydroxyphenylthio)-3,3-dimethylpropyl]-1-oxa-2-oxo-3,8-diazaspiro-[4.5]decane or its hydrochloride.

8. A pharmaceutical composition comprising as active ingredient a compound according to claim 1 together with one or more suitable pharmaceutically-acceptable excipients or diluents.

9. A method for treating a mammal afflicted with an atherosclerotic condition characterized by membrane lipid peroxidation comprising the step of administering to the said mammal an antioxidative amount of a compound of claim 1 which is effective for alleviation of the said atherosclerotic condition.

* * * * *

UNITED STATES PATENT AND TRADEMARK OFFICE
CERTIFICATE OF CORRECTION

PATENT NO. : 5,206,247

DATED : Apr. 27, 1993

INVENTOR(S) : Gilbert Regnier, Claude Guillonneau, Jean-Paul Vilaine, Albert Lenaers, Jean-Pierre Iliou It is certified that error appears in the above-identified patent and that said Letters Patent is hereby corrected as shown below:

Column 16, line 10; "peroxidation comprising" should read
-- peroxidation, comprising --. (R&A 8-27-92, P. 1)

Signed and Sealed this

Twenty-sixth Day of April, 1994

Attest:

BRUCE LEHMAN

*Attesting Officer*     *Commissioner of Patents and Trademarks*